United States Patent [19]

Kaminsky et al.

[11] Patent Number: 4,544,762
[45] Date of Patent: Oct. 1, 1985

[54] PROCESS FOR THE PREPARATION OF OLIGOMERIC ALUMINOXANES

[75] Inventors: Walter Kaminsky, Pinneberg; Heinrich Hähnsen, Delingsdorf, both of Fed. Rep. of Germany

[73] Assignee: Hoechst Aktiengesellschaft, Fed. Rep. of Germany

[21] Appl. No.: 546,862

[22] Filed: Oct. 31, 1983

[30] Foreign Application Priority Data

Nov. 2, 1982 [DE] Fed. Rep. of Germany ....... 3240383

[51] Int. Cl.$^4$ .................................................. C07F 5/06
[52] U.S. Cl. ...................................... 556/179; 556/175; 556/187; 526/352; 585/502
[58] Field of Search ........ 260/448 A, 448 AD, 448 R

[56] References Cited

U.S. PATENT DOCUMENTS

| | | | |
|---|---|---|---|
| 2,952,695 | 9/1960 | Stedehouder et al. | 260/448 R X |
| 2,979,497 | 4/1961 | Rinse | 260/448 R X |
| 3,054,816 | 9/1962 | Rinse | 260/448 AD |
| 3,055,847 | 9/1962 | Woods et al. | 260/448 AD |
| 3,657,149 | 4/1972 | Vandenberg | 260/448 A X |
| 4,055,634 | 10/1977 | Brenner et al. | 260/448 A X |

OTHER PUBLICATIONS

Mole et al., Organoaluminum Compounds, Elsevier Publ. Co., N.Y., pp. 211–215, 224–228, (1972).
Nesmeyanov et al., The Organic Compounds of Boron, Aluminum, Gallium, Indium and Thallium, North-Holland Publ. Co., Amsterdam, pp. 456–458, 474–481, (1967).

*Primary Examiner*—Helen M. S. Sneed
*Attorney, Agent, or Firm*—Connolly and Hutz

[57] ABSTRACT

The present invention relates to a process for the preparation of oligomeric alkylaluminoxanes of the general formulae:

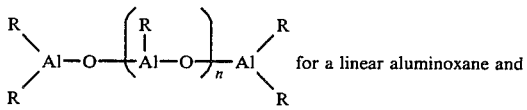

for a linear aluminoxane and

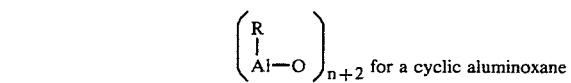 for a cyclic aluminoxane in which R=$C_1$-$C_6$-alkyl, preferably methyl, and n=2–40, preferably 10–20, by reacting aluminum salts containing water of crystallization, preferably aluminum sulfate containing water of crystallization, with an aluminum trialkyl, preferably aluminum trimethyl. Aluminoxanes of this type can be used as a catalyst component in the preparation of high-activity, homogeneous Ziegler catalysts.

12 Claims, No Drawings

PROCESS FOR THE PREPARATION OF OLIGOMERIC ALUMINOXANES

The present invention relates to the preparation of aluminoxanes, preferably methylaluminoxane. Aluminoxanes of this type can be used as a component of catalysts in the preparation of high-activity, homogeneous Ziegler catalysts, as is described, for example, in German Patent Application Nos. P 30 07 725.9 and P 31 27 133.2.

Various processes are known for the preparation aluminoxanes. Thus, aluminoxanes are obtained, for example, by the action of steam on a benzene solution of a trialkylaluminum (J. A. Chem. Soc. 90, 1968, 3173), by using lithium dialkylaluminate as the organoaluminum starting compound (J. Chem. Soc. 89, 1967, 173), by oxidizing aluminum-hydrocarbon compounds with lead dioxide (J. Organomet. Chem. 43, 1972, 81) and also be hydrolyzing aluminum alkyls with copper sulfate containing water of crystallization (Jzv. Akad. Nauk, USSR, Ser. Chim. 11, 1975, 2547), and also, in general, with salts containing water of crystallization of the formula C A aH$_2$O (C=cation, A=anion and a=2; USSR Pat. No. 566,844), and also by adding water slowly to aluminum alkyls (U.S. Pat. No. 3,242,099). In all these processes, very short-chain aluminoxanes are obtained, which are predominantly or exclusively compounds of the formula

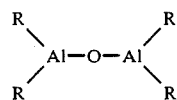

in which R=methyl, ethyl, butyl, isobutyl and the like. Additionally, methylaluminoxane can only be prepared with difficulty and in a very poor yield by the methods mentioned.

It is also known to prepare oligomeric mixtures of aluminoxanes having a degree of oligomerization between 2 and 12 by reacting trimethylaluminum with copper sulfate containing water of crystallization (CuSO$_4$.5H$_2$O) in accordance with a method of J. Herwig (thesis, Hamburg University, 1979). However, in this case the yield is only approx. 30%, relative to the aluminum trialkyl employed. A further disadvantage is that, as a result of reduction reactions, traces of copper always remain in the aluminoxane thus prepared, and these color the product yellow to red. Before being used as a component of the catalyst in the polymerization of olefins, it must be filtered, purified and recrystalized, since otherwise the polymerization is interfered with and the quality of the polymer is adversely affected. However, even after purification and recrystallization, these aluminoxanes can still contain residues of copper.

It has now been found that longer-chain, oligomeric, linear and/or cyclic alkylaluminoxanes of the formulae

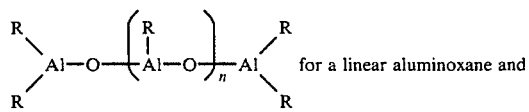 for a linear aluminoxane and

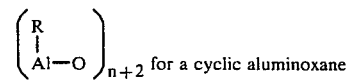 for a cyclic aluminoxane wherein n is 2–40, preferably 10–20 and R is C$_1$–C$_6$-alkyl, preferably methyl, are obtained if an aluminum trialkyl, preferably aluminum trimethyl, dissolved in an inert aliphatic or aromatic solvent, preferably toluene or heptane, is reacted, at temperatures between −20° and 100° C., preferably between 15° and 40° C., with aluminum salts, preferably aluminum sulfate, containing water of crystallization.

In this reaction, the ratio by volume between the solvent and the aluminum alkyl used is 1:1 to 50:1—preferably 5:1—and the reaction time, which can be checked by the elimination of the alkane, is 1 to 200 hours, preferably 10 to 40 hours.

The aluminum salts containing water of crystallization which are used are preferably those which have a high content of water of crystallization. Hydrated aluminum sulfate, above all the compound Al$_2$(SO$_4$)$_3$.18H$_2$O and Al$_2$(SO$_4$)$_3$.16H$_2$O, having the particularly high content of water of crystallization of 16 and 18 mole, respectively, of H$_2$O per mole of Al$_2$(SO$_4$)$_3$ is particularly preferred.

It is particularly preferrable to employ aluminum trimethyl as the aluminum alkyl. Other examples of suitable aluminum alkyls are the compounds AlR$_3$ in which R is ethyl, isopropyl, butyl, isobutyl and phenyl.

Aluminum trimethyl which has been diluted with an inert solvent, for example heptane or toluene, reacts with the Al$_2$(SO$_4$)$_3$.18H$_2$O or Al$_2$(SO$_4$)$_3$.16H$_2$O which are used particularly preferentially in accordance with the equation:

$$x \cdot (Al_2(SO_4)_3 \cdot 18(16)H_2O) + (n + 1)Al(CH_3)_3 \longrightarrow$$

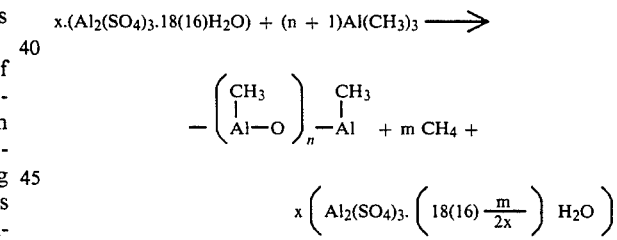

in which n=2 to 40, preferably 10–20, m=2n for linear aluminoxanes or 2n+2 for cyclic aluminoxanes and x=0.06n to 0.15n, preferably 0.11n.

When hydrated aluminum sulfate, which is readily accessible, is reacted with aluminum trimethyl, it is possible, surprisingly, to increase the yield of methylaluminoxane to over 60% and to increase the average degree of oligomerization to values of more than 20. The methylaluminoxane thus prepared is colorless and free from other metals which exert an adverse affect, for example when it is used as a co-catalyst for olefin polymerization.

Compared with the processes of the state of the art, the process according to the invention has substantial advantages which can be seen, above all, in the fact that a higher yield is achieved and that aluminoxanes of greater purity and a higher degree of oligomerization are obtained. This makes it possible also to use the aluminoxane solution prepared in accordance with the invention direct, without the filtration, purification and recrystallization required in the processes of the state of the art, for example to use it as a co-catalyst together with a heavy metal component in the polymerization of olefins. However, it is probably preferable in some cases to separate the aluminoxanes prepared in accordance with the invention from the hydrocarbon solution and to subject them to recrystallization and to purification. It is also possible to work up the aluminoxane solution to give solid aluminoxane.

As already mentioned, the longer-chain alkylaluminoxanes, above all methylaluminoxane, which have been prepared in accordance with the invention can be used advantageously as a catalyst component in the polymerization of olefins. It is of decisive importance in this connection that the degree of oligomerization of these aluminoxanes should be substantially higher than 2. Short-chain aluminoxanes, such as the methylaluminoxane $(CH_3)_2Al-OAl(CH_3)_2$ known from the state of the art, produce, together with a heavy metal component, catalyst systems which have only a very slight polymerization activity or virtually none.

On the other hand, catalysts which are soluble in many hydrocarbons and which enable extremely high activities exceeding 25 million g of polyethylene per g of transition metal and per hour to be achieved in the polymerization of olefins are obtained, for example, by mixing methylaluminoxane prepared in accordance with the invention and bis-(cyclopentadienyl) compounds of titanium and especially zirconium. In addition, catalyst systems containing the longer-chain methylaluminoxanes as the co-catalyst are fairly insensitive towards impurities in, for example, the monomers.

It is also an advantage that the aluminoxanes according to the invention are less spontaneously inflammable and have a less corrosive effect than the aluminum alkyl halides which are frequently used as the co-catalyst in the polymerization of olefins.

EXAMPLE 1

37.1 g of $Al_2(SO_4)_3.18H_2O$ (0.056 mole, corresponding to 1 mole of $H_2O$) were suspended in 250 ml of toluene, 50 ml of trimethylaluminum (0.52 mole) were added and the reaction was carried out at 20° C. After a reaction time of 30 hours, approx. 1 mole of methane had been evolved. The solution was then freed from the solid aluminum sulfate by filtration. On removing the toluene, 19.7 g of methylaluminoxane were obtained. The yield was 63% of theory. The average molecular weight, determined cryoscopically in benzene, was 1,170. The number of

units was found by calculation to be 20.2.

The average degree of oligomerization was approx. 15.

EXAMPLE 2

The procedure was as in Example 1, but the reaction was carried out at a temperature of 40° C. After only 11 hours, 1 mole of methane had been split off. The solution was filtered and used direct as a stable co-catalyst solution for the production of the soluble Ziegler catalyst. Yield of methylaluminoxane 60%.

EXAMPLE 3

A procedure analogous to that of Example 1 was used, but with the modification that heptane was used as the solvent and the reaction temperature was 15° C. 40 hours were required to split off 1 mole of methane. The reaction mixture, which contained the methylaluminoxane and aluminum sulfate, was suitable, even without filtration, to form a highly active Ziegler catalyst when biscyclopentadienylzirconium compounds were added. Part of the batch was worked up to give pure aluminoxane, which had an average molecular weight of 1,210, determined cryoscopically. The number of

units was calculated to be 20.9. The average degree of oligomeration was approx. 16.

EXAMPLE 4

60 g of hydrated aluminum chloride $AlCl_3.6H_2O$ were suspended in 150 ml of toluene, a solution of 50 ml (0.52 mole) of trimethylaluminum was added and the mixture was reacted for 75 hours at 40° C. When one mole of methane had been evolved (66% conversion), the suspension was filtered and the methylaluminoxane was obtained from the filtrated by removing the solvent (yield 18.4 g). The aluminoxane had an average molecular weight of 1,000, determined cryoscopically.

EXAMPLE 5

47 g of hydrated aluminum nitrate $Al(NO_3)_3.9H_2O$ were suspended in toluene as in Example 4, and trimethylaluminum was added. After a reaction time of 45 hours at 30° C., the mixture was filtered and the filtrate was worked up to give methylaluminoxane, which had a slight brown color (yield 18.4 g).

EXAMPLE 6

45 g of $Al_2(SO_4)_3.16H_2O$ were suspended in 150 ml of toluene and reacted at 40° C. with 65 ml (0.47 mole) of aluminum triethyl, dissolved in 100 ml of toluene. The elimination of ethane took place more rapidly than the elimination of methane in the comparable methyl system. Thus, it was possible to discontinue the reaction after a reaction time of only 6 hours, when 1 mole of ethane had been evolved, and to work up the filtrate to give ethylaluminoxane. The yield was 18 g of colorless, solid ethylaluminoxane. The molecular weight, determined cryoscopically, was 1,511. This corresponds to approx. 21 aluminum units in a molecule of aluminoxane.

We claim:

1. A process for the preparation of oligomeric, linear and/or cyclic alkylaluminoxanes of the formulae:

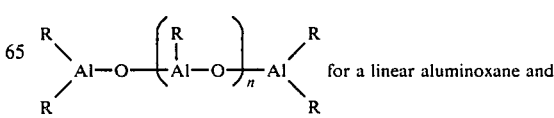

for a linear aluminoxane and

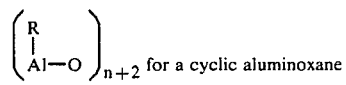 for a cyclic aluminoxane in which n=2 to 40 and R=$C_1$-$C_6$-alkyl, which comprises reacting, with the elimination of an alkane, an aluminum trialkyl dissolved in an inert aliphatic or aromatic solvent at temperatures between −20° and 100° C. with an aluminum salt containing water of crystallization.

2. The process as claimed in claim 1, wherein toluene or heptane is used as the solvent.

3. The process as claimed in claim 1, wherein the reaction is carried out at temperatures between 15° and 40° C.

4. The process as claimed in claim 1, wherein aluminum trimethyl is employed as the aluminum trialkyl.

5. The process as claimed in claim 1, wherein 1 to 30% strength solutions of aluminum trimethyl are used.

6. The process as claimed in claim 1, wherein 5 to 20% strength solutions of aluminum trimethyl are used.

7. The process as claimed in claim 1, wherein aluminum sulfate is used as the aluminum salt containing water of crystallization.

8. The process as claimed in claim 1, wherein hydrated aluminum sulfates containing 9 to 18 molecules of water of crystallization are used as the aluminum salt containing water of crystallization.

9. The process as claimed in claim 1, wherein $Al_2(SO_4)_3.18H_2O$ or $Al_2(SO_4)_3.16H_2O$ is used as the aluminum salt containing water of crystallization.

10. The process as claimed in claim 1, wherein aluminum trimethyl is used as the aluminum trialkyl and hydrated aluminum sulfate is used as the aluminum salt containing water of crystallization, and the molar ratio between aluminum trimethyl and hydrated aluminum sulfate is 2 to 18.

11. The process as claimed in claim 1, wherein aluminum trimethyl is used as the aluminum trialkyl and hydrated aluminum sulfate is used as the aluminum salt containing water of crystallization, and the molar ratio between aluminum trimethyl and hydrated aluminum sulfate is 9.

12. The process as claimed in claim 1, wherein aluminum trimethyl is employed as the aluminum trialkyl, and the reaction mixture is filtered and the filtrate is worked up to give solid methyl aluminoxane by removing the solvent.

* * * * *